United States Patent [19]
Hollingsworth et al.

[11] Patent Number: 6,114,566
[45] Date of Patent: Sep. 5, 2000

[54] 4-CYANO-3-HYDROXYBUTANOYL HYDRAZINES, DERIVATIVES AND PROCESS FOR THE PREPARATION THEREOF

[75] Inventors: Rawle I. Hollingsworth, Haslett; Guijun Wang, East Lansing, both of Mich.

[73] Assignee: Board of Trustees Operating Michigan State University, East Lansing, Mich.

[21] Appl. No.: 09/317,398

[22] Filed: May 24, 1999

[51] Int. Cl.⁷ ..................................................... C07C 243/28
[52] U.S. Cl. ............................................ 558/445; 558/451
[58] Field of Search ...................................... 558/445, 451

[56] References Cited

U.S. PATENT DOCUMENTS 5,292,939  3/1994  Hollingsworth .

OTHER PUBLICATIONS

Goa, K. L., et al., Drugs 34, 1 (1987).
Guarnieri, G., et al., Amer. J. Clin. Nutri. 33, 1489 (1980).
Thomsen, J. H., et al., Amer. J. Cardiol. 33, 300 (1979).
Chapoy, P.R., et al., New Eng. J. Med. 303, 1389 (1980).
Takano, S., et al., Tetrahedron Lett, 28, 1783 (1987).
Comber, R. N., et al., J. Org. Chem. 52:2311 (1987).
Fuganti, C., et al., Tetrahedron Lett. 27:2061 (1986).
Kulla, H. G., Chimia, 45, 81 (1991).
Kasai, N., et al., Tetrahedron Lett. 33, 1211 (1992).
Hashiguchi, S., et al., Synthesis, 403 (1992).
Lu, Y., et al., Tetrahedron Asymmetry 1, 707 (1990).
Bianchi, D., et al., J. Org. Chem. 53, 104 (1988).
Gopalan, A. S., et al., Tetrahedron Lett. 25, 5235 (1984).
Bols, M., et al., Tetrahedron Lett. 48:319 (1992).
Bellamy, F. C., et al., Tetrahedron Lett. 31, 7323 (1990).
Rajashekhar, B., et al., J. Org. Chem. 50, 5480 (1985).
Bose, D. S., et al., Synth. Commun. 19, 3313 (1989).
Pellegata, R., et al., Tetrahedron Lett. 41, 5607 (1985).
Bock, K., et al., Acta Chem. Scand. Ser. B37, 341 (1983).
Jung, M. E., et al., J. Am. Chem. Soc. 102, 6304 (1980).
Kolb, H. C., et al., Tetrahedron Asymmetry 4, 133 (1993).
Braun, M., et al., Synthesis, 856 (1989).
Rossiter, B.E., et al., J. Org. Chem. 49, 3707 (1984).
Kabat, M.M., et al., Tetrahedron Asymmetry 8 2663 (1997).
Lohray, B.B., et al., Tetrahedron Asymmetry 8, 633–638 (1997).
Bernabei, I., et al., Chem. Eur. J. 2, 826 (1996).
Kitamura, M., et al., Tetrahedron Lett., 29, 1555 (1988).
Sakuraba, S., et al., Chem. Pharm. Bull. 43, 738 (1995).
Hollingsworth, R.I., Biotech. Ann. Rev. 2, 281 (1996).
Huang, G., et al., Tetrahedron, 54, 1355 (1998).
Wang, G., et al., J. Org. Chem. 64 1036 (1999).
Brower, P. L., eta l., Tetrahedron Lett. 33 2279 (1992).
Breuilles, P., et al., Tetrahedron Lett. 35 1401 (1994).
Almond, M.R., et al., Organic Syntheses 8 132 (1993).
Leclerc, R., et al., Tetrahedron Lett. 35 1999 (1994).
Jung, M.E., et al., J. Sm. Chem. Soc. 102 6304 (1980).
Kaneko, T., et al., Bull. Chem. Soc. Japan 35 1153 (1962).
Jurczak, J., et al., Tetrahedron 42 447 (1986).

*Primary Examiner*—Robert Gerstl
*Attorney, Agent, or Firm*—Ian C. McLeod

[57] ABSTRACT

Novel 4-cyano-3-hydroxybutanoyl hydrazides (10), particularly R-chiral intermediates are described. The intermediates are useful in preparing (R)-3-hydroxy-4-trimethylaminobutyric acid (L-carnitine) and R-4-amino-3-hydroxybutyric acid (GABOB) and chiral chemical intermediates which are medically useful.

9 Claims, 4 Drawing Sheets

1

2

3

4

3A

SCHEME 1

SCHEME 2

SCHEME 3

4-CYANO-3-HYDROXYBUTANOYL HYDRAZINES, DERIVATIVES AND PROCESS FOR THE PREPARATION THEREOF

CROSS-REFERENCE TO RELATES APPLICATIONS

None.

STATEMENT REGARDING FEDERALLY SPONSORED RESEARCH OR DEVELOPMENT

This invention was made with Department of Energy support under Grant No. DE-FG02-89ER14029. The government has certain rights in the invention.

BACKGROUND OF THE INVENTION

(1) Field of the Invention

The present invention relates to the preparation of novel 4-cyano-3-hydroxybutanoyl hydrazides which are intermediates to the preparation of medicinally important chiral compounds particularly (R)-3-hydroxy-4-trimethylaminobutyric acid (L-carnitine) and (R)-4-amino-3-hydroxy butyric acid (GABOB). In particular the present invention relates to the preparation of chiral compounds.

(2) Description Of Related Art (R)-3-hydroxy-4-trimethylaminobutyric acid (L-carnitine 1 and (R)-4-amino-3-hydroxy-butyric acid (GABOB) 2 (FIGS. 1A and 1B) have a very high level of medical significance. L-carnitine is a very important intermediate in lipid biosynthesis. It functions as a carrier for transporting fatty acids into mitochondria for oxidation. Since fatty acid oxidation is a critical step by which cells derive energy, carnitine is important for cellular energetics. Deficiencies in the biosynthesis of L-carnitine lead to severe neurological problems. The two major uses of L-carnitine are in sports medicine and infant nutrition. There are several medical indications for which L-carnitine can be prescribed (Goa, K. L., et al. Drugs 34, 1 (1987); Guarnieri, G., et al., Amer. J. Clin. Nutr. 33, 1489 (1980); and Thomsen, J. H., et al., Amer. J. Cardiol. 33, 300 (1979)). (R)-4-Amino-3-hydroxy-butyric acid (GABOB) is a well known drug substance that functions as an agonist of gamma aminobutyric acid (GABA). It has been demonstrated to be effective in managing a variety of clinical conditions including schizophrenia and other character-based illnesses (Chapoy, P. R., et al., New Engl. J. Med. 303, 1389 (1980); and Takano, S., et al., Tetrahedron Lett, 28, 1783 (1987)), epilepsy and other illnesses that result in severe convulsions (Pinelli, P., Farmaco, Ed. Sci. 25, 187 (1970); and Demaio, D., et al., Acta Neurol. 16, 366 (1961)). Its use for the correction of some clinical conditions observed in children has also been explored (Buscaino, G. A., et al., Acta Neurol. 16, 748 (1961); and Comber, R. N., et al., J. Org. Chem. 52:2311 (1987)), fermentation (Fuganti, C., et al., Tetrahedron Lett, 27: 2061 (1986); Kulla, H. G., Chimia, 45, 81 (1991); Kasai, N., et al., Tetrahedron Lett. 33, 1211 (1992); Hashiguchi, S., et al., Synthesis 403 (1992); Lu, Y, et al., Tetrahedron Asymmetry 1 707 1990); Bianchi, D., et al., J. Org. Chem. 53, 104 (1988); Gopalan, A. S., et al., Tetrahedron Lett. 25, 5235 (1984)), asymmetric synthesis from natural products (Bols, M., et al., Tetrahedron Lett. 48:319 (1992); Bellamy, F. D., et al., Tetrahedron Lett, 31, 7323 (1990); Rajashekhar, B., et al., J. Org. Chem. 50, 5480 (1985); Bose, D. S., et al., Synth. Commun. 19, 3313 (1989); Pellegata, R., et al., Tetrahedron Lett. 41, 5607 (1985); Bock, K., et al., Acta Chem. Scand. Ser. B37, 341 (1983); Jung, M. E., et al., J. Am. Chem. Soc. 102, 6304 (1980)), and catalytic asymmetric synthesis (Kolb, H. C., et al., Tetrahedron Asymmetry 4, 133 (1993); Bubnov, Y. N., et al., Mendeleev Commun. 86 (1992); Braun, M., et al., Synthesis, 856 (1989); Rossiter, B. E., et al., J. Org. Chem. 49, 3707 (1984); Kabat, M. M., et al., Tetrahedron Asymmetry 8 2663 (1997); Lohray, B. B., et al., Tetrahedron Asymmetry 7, 2411 (1997); Bernabei, I., et al., Chem. Eur. J. 2, 826 (1996); Kitamura, M., et al., Tetrahedron Lett., 29, 1555 (1988); Sakuraba, S., et al., Chem. Pharm. Bull, 43, 738 (1995)). There is still a need, however, for straightforward syntheses that have significant practical value.

(S)-3-Hydroxy-γ-butyrolactone 3 (FIG. 1C) is a 4-carbon chiral intermediate that can be obtained in high yield and very high chiral purity from a variety of carbohydrate building blocks including lactose, maltose and maltodextrins (Hollingsworth, R. I., Biotech. Ann. Rev. 2, 281 (1996); Huang, G., et al., Tetrahedron, 54 1355 (1998); and Hollingsworth, R. I., U.S. Pat. No. 5,292,939 (1994)). The functionalities present in this molecule make it easily amenable to conversion to carnitine and GABOB by placing a trimethylammonium group in the 4-position after ring opening the lactone with hydrogen bromide to form the 4-bromo acid 3A (FIG. 1E) and then displacing the bromo group with trimethylamine. However, the configuration at the 3-position is not the desired one. Synthesizing these molecules with the correct configuration from (S)-3-hydroxy-γ-butyrolactone requires inversion of the 3-hydroxyl group or some equivalent transformation. Because of its position relative to the carbonyl group, attempts at inverting the 3-hydroxyl group by activation and displacement readily leads to elimination to yield 2-(5H) furanone. The alcohol group could not be modified even under the mildest of basic conditions. It was therefore necessary to provide an alternative to the inversion reaction.

OBJECTS

It is therefore an object of the present invention to provide a novel process leading to the production of L-carnitine 1, (R)-3-hydroxy-4-trimethylaminobutyric acid, and GABOB 2, (R)-4-amino-3-hydroxybutyric acid. In particular the present invention relates to novel intermediate compounds leading to the production of the compounds 1 and 2. Further, it is an object of the present invention to provide a process which is economically favorable and relatively easy to perform. These and other objects will become increasingly apparent by reference to the following description and the drawings.

SUMMARY OF THE INVENTION

The present invention relates to novel compounds which are 4-cyano-3-hydroxybutanoyl hydrazide. In particular the present invention relates to the compound R-4-cyano-3-hydroxybutanoyl hydrazide.

The present invention also relates to a process for the preparation of 4-cyano-3-hydroxybutanoyl hydrazide which comprises: reacting 4-cyano-3-hydroxybutyric acid alkyl ester, where alkyl contains 1 to 6 carbon atoms, with anhydrous hydrazine in a polar organic solvent to produce the 4-cyano-3-hydroxybutanoyl hydrazide in a reaction mixture; and separating the 4-cyano-3-hydroxybutanoyl hydrazide from the reaction mixture to produce the 4-cyano-3-hydroxybutanoyl hydrazide. The present invention also relates to a process for the preparation of 4-cyano-3-hydroxybutanoyl hydrazide which comprises: reacting 4-cyano-3-hydroxybutyric acid alkyl ester, where alkyl contains 1 to 6 carbon atoms, with anhydrous hydrazine in absolute ethanol in the absence of water to produce the 4-cyano3-hydroxybutanoyl hydrazide in a reaction mixture as a precipitate; and separating the precipitate from the reaction mixture to produce the 4-cyano-3-hydroxybutanoyl hydrazide.

The present invention further relates to a process for the preparation of 4-amino-3-hydroxynitrile which comprises: reacting 4-cyano-3-hydroxy butyric acid alkyl ester, where alkyl contains 1 to 6 carbon atoms, with anhydrous hydrazine in a polar organic solvent to produce 4-cyano-3-hydroxybutanoyl hydrazide in a reaction mixture; separating the 4-cyano-3-hydroxybutanoyl hydrazide from the reaction mixture to produce the 4-cyano-3-hydroxybutanoyl hydrazide; and reacting 4-cyano-3-hydroxybutanoyl hydrazide with a decarboxylation and rearrangement agent to produce the 4-amino-3-hydroxybutyronitrile as a salt in a reaction mixture; and separating the 4-amino-3-hydroxybutyronitrile as a salt from the reaction mixture.

Finally the present invention relates to a process for the preparation of 4-amino-3-hydroxybutyronitrile which comprises: reacting 4-cyano3-hydroxy butyric acid alkyl ester, where alkyl contains 1 to 6 carbon atoms, with anhydrous hydrazine in absolute ethanol in the absence of water to produce 4-cyano-3-hydroxybutanoyl hydrazide in a reaction mixture as a precipitate; separating the precipitate from the reaction mixture to produce the 4-cyano-3-hydroxybutanoyl hydrazide; and reacting 4-cyano-3-hydroxybutanoyl hydrazide with nitrous acid to produce the 4-amino-3-hydroxybutyronitrile as a salt in a reaction mixture; and separating the 4-amino-3-hydroxybutyronitrile as a salt from the reaction mixture.

DESCRIPTION OF PREFERRED EMBODIMENTS

Figure 1A:
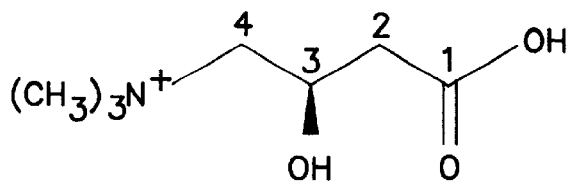
FIGS. 1A to 1E show the various structures of the present invention.
Figure 1B:
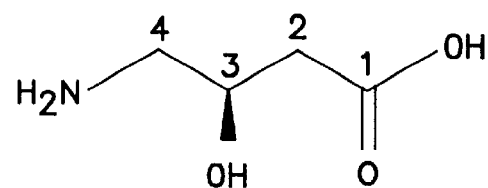
Figure 1C:
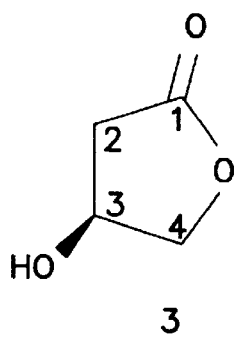
Figure 1D:
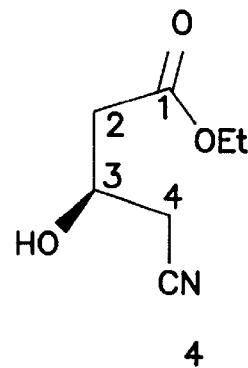
Figure 1E:
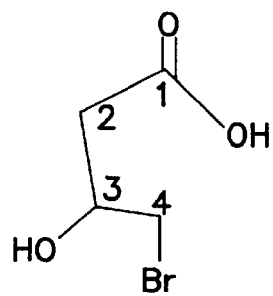

A straightforward route is described to L-carnitine 1 and (R)-3-hydroxy-4-trimethylaminobutyric acid 2 starting from (S)-3-hydroxy-γ-butyrolactone 3 by adding a highly oxidized carbon at one end whilst removing one carbon from the other thus switching the functional group priorities. In this method, the lactone 3 is transformed to an (R) 4-cyano-3-alkoxyoxybutyrate ester 4 which is then converted to the novel acyl hydrazide by treatment with hydrazine, which readily converted to the (R)-4-amino-3-hydroxybutyronitrile 8, a precursor of L-carnitine 1 and GABOB 2, by a Curtius rearrangement under conditions that do not result in deamination.

The present invention switches the priorities of the 1-and 4-position in the 4-carbon intermediate represented by (S)-3-hydroxy-γ-butyrolactone 4. This requires removal of the 1-carbon and addition of a new high-priority carbon at the 4-position. This was obtained either by removing the 1-carbon first then adding one more carbon at the 4-position, or introducing one more carbon to the 4-position then removing the 1-carbon. The first approach has been already described (Wang, G., et al., J. Org. Chem., 64 1036 (1999). Here we describe the second approach.

The lactone 3 (FIG. 2, Scheme 1) was transformed to (R) 4-cyano-3-hydroxybutyric acid ethyl ester 4, a very useful synthetic intermediate which has been used for the synthesis of other natural products such as HMG-coA reductase inhibitors (Brower, P. L., et al., Tetrahedron Lett., 33 2279 (1992)). The nitrile ester 4 is commercially available. HMG-coA reductase is the rate limiting enzyme in cholesterol biosynthesis. In an earlier preparation of the nitrile ester 4 (Brower, P. L., Tetrahedron Lett. 33, 2279 (1992)), (S) 4-bromo-3-hydroxybutyric acid ethyl ester 5 was an intermediate and was prepared from ascorbic acid by a very circuitous route. Here nitrile ester 4 was prepared from lactone 3 simply by treatment with HBr in acetic acid followed by deacylation of the acetylated bromo hydroxyacid with acidic ethanol. This also converted the acid to an ethyl ester group.

Figure 2:
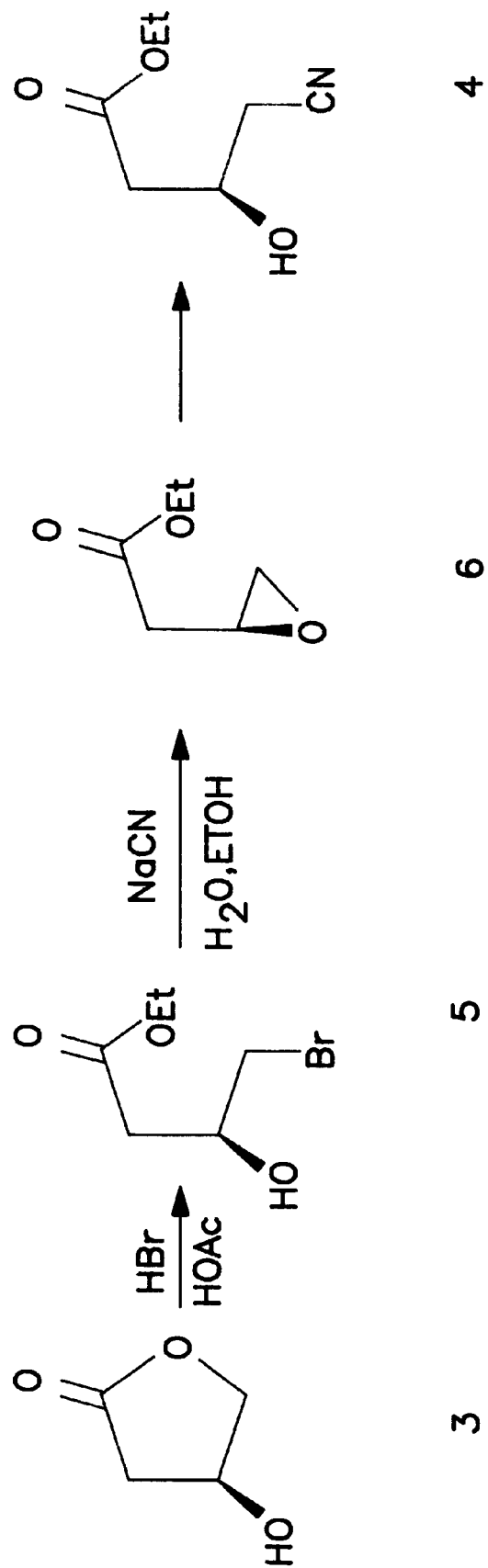
FIG. 2 shows Scheme 1 for the synthesis of cyano ester 4 from 3-hydroxy-γ-butyrolactone 3.

In the preparation of the nitrile ester 4, Scheme 1, FIG. 2, the ester group can be a lower alkyl group containing 1 to 6 carbon atoms. The ethyl ester is preferred.

In a first attempt (FIG. 3, Scheme 2), the ester 4 was transformed to the corresponding amide 8A by treatment with ammonia in methanol solution. Interestingly, attempts using aqueous ammonia gave a complex mixture of products. An attempt to convert the amide group in compound 1 to an amino group by Hoffman rearrangement using hypochlorite failed. 3-Hydroxypentanedioic acid 9 was obtained instead. Protecting the free hydroxyl group in the amide 7 with a variety of functional groups such as methoxymethyl ether and methoxyisopropyl ether also did not result in a successful transformation. In each case the nitrile group in compound 7 was hydrolyzed to a carboxylic acid function. The intermediate amide 7 (Breuilles, P., et al., Tetrahedron Lett. 35 1401 (1994)) has been converted to R-carnitine by other Hoffman rearrangement reagents such as I, I-bis-trifluoroacetyloxy-iodobenzene (Almond, M. R., et al., Organic Syntheses 66 132 (1988); and Leclerc, R., et al., Tetrahedron Lett. 35 1999 (1994)). The reagents for this transformation are expensive and this method is therefore not very practical on a commercially relevant scale.

Figure 4:
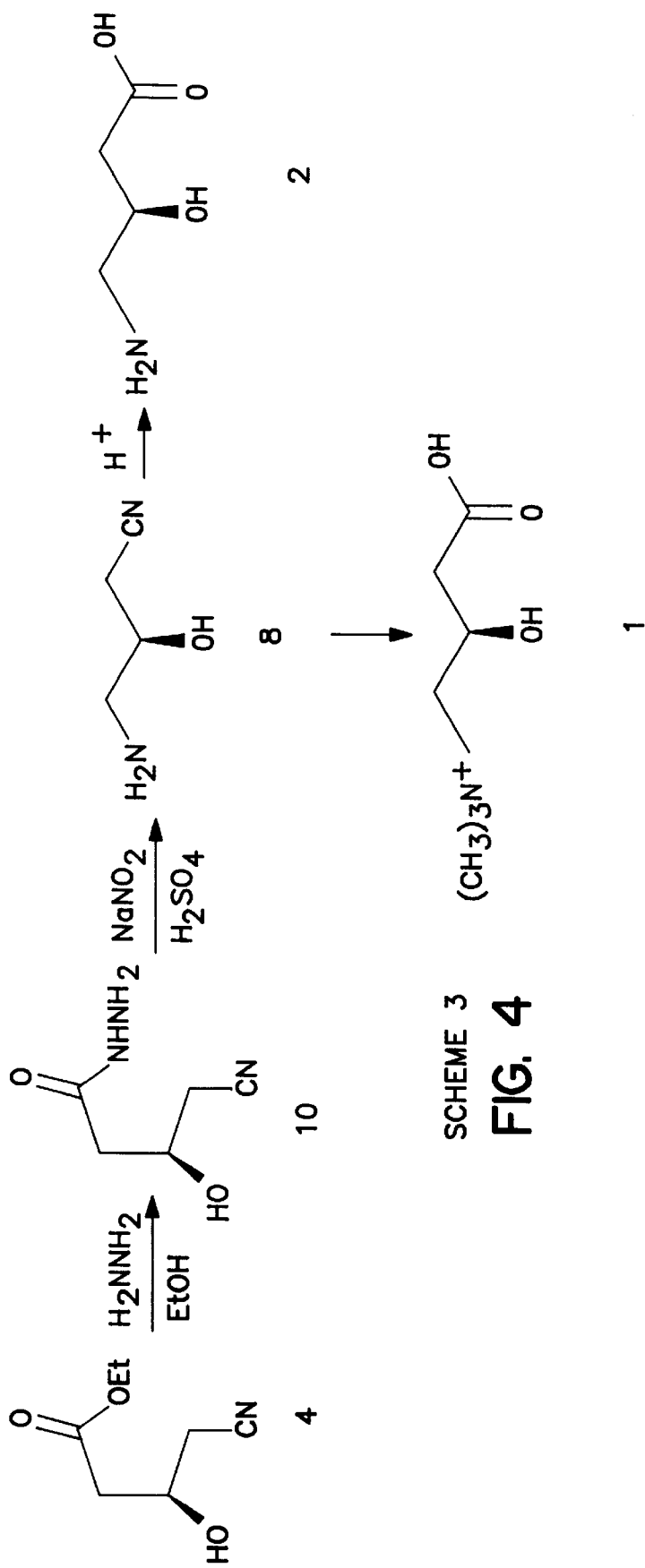
FIG. 4 shows Scheme 3 for the synthesis to L-carnitine and R-GABOB by the process of the present invention.

A Curtius type reaction avoids the oxidative alkaline conditions that characterize the Hoffman reaction described previously. There was the possibility, however, that the amino group, once formed would be further deaminated to give a hydroxyl group. The reaction successfully gave the desired product in a short simple sequence (FIG. 4, Scheme 3). The conversion was carried out by treating the cyano ester 4 with hydrazine. The resulting acyl hydrazide 10 was then treated with sodium nitrite and sulfuric acid at 60° C. for 16–18 hours. This reaction was followed by $^1$H-NMR spectroscopy.

The conditions for the hydrazide preparation:

The reagents for the hydrazide preparation, besides anhydrous hydrazine ($H_2NNH_2$) the hydrazine hydrate can also be used.

The reaction can be carried out from room temperature to refluxing condition. Alcoholic solvent is preferred.

The acyl hydrazide 10 is a white crystalline material that is quite stable at room temperature for several weeks to a few months if kept away from light. The conversion from this hydrazide to the cyano amine 8 proceeded in excellent conversion (>95%). The resulting cyano-amine 8 was converted to GABOB 2 by refluxing it with an acid and also to carnitine by methylation followed by hydrolysis of the cyano group (Fuganti, C., et al., Tetrahedron Lett. 27 2061 (1986); and Jung, M. E., et al., J. Sm. Chem. Soc. 102 6304 (1980)). These conversions are straightforward and well documented in the literature (Kaneko, T., et al., Bull. Chem. Soc. Japan 35 1153 (1962) and Jurczak, J., et al., Tetrahedron 42 447 (1986)).

The process of the present invention provides a general route to L-carnitine 1 or (R)-GABOB 2 and indeed other 4-carbon chiral compounds, such as hydroxypyrrolidinones (from the cyclization of GABOB), from a readily available chiral material with the undesirable enantiochemistry. The route utilizes an intermediate cyanoester 4, that is already a desired material, for use in the synthesis of other drug substances to prepare a new stable intermediate, 4-cyano-3-hydroxy-butanoic acid hydrazide 10. The conversion of intermediate 8 to carnitine and GABOB is simple and straightforward and the starting lactone 3 material is readily available from carbohydrates such as maltose and lactose on large scale. The route brings about an effective inversion at the chiral center by switching the priorities of two groups, thus overcoming the stereochemical bias in the hexose pool and circumventing the difficult elimination problems that attend a direct inversion.

In the preparation of 4-cyano-3-hydroxybutanoyl hydrazide 10, the reaction is conducted in a polar solvent that does not react with hydrazine, preferably a polar organic solvent in which hydrazide 10 is insoluble. The reaction is preferably anhydrous so that hydrazide 10 precipitates from the solvent. If water is present then hydrazide 10 can be obtained by removal of the solvent and excess hydrazine by concentration under reduced pressure. Preferred solvents for the reaction are lower alkanols containing 1 to 6 carbon atoms. Absolute ethanol is the most preferred.

Preferably there is an excess of hydrazine in the reaction mixture; most preferably 1.5 times equivalents or more. An excess of more than two (2) times equivalents of hydrazine is unnecessary and wasteful. The reaction is conducted at 0° to 50° C.; however room temperature is preferred.

In the production of 4-amino-3-hydroxybutyronitrile 8 from hydrazide 10 the reaction is preferably conducted in the presence of nitrous acid which served as the decarboxylation and rearrangement agent. In an alternative method, the intermediate isocyanate was isolated by extraction with ether. It was then hydrolyzed with trifluoroacetic acid to give the desired amine product via the trifluoroacetamide. This removes completely the possibility of deamination of the product by any excess nitrous acid present. Any strong acid can be used with sodium nitrite to produce the acidic nitrous acid. Preferred is concentrated sulfuric acid. The nitrous acid is used in an equivalent excess, preferably at least about 1.5 times equivalents. The reaction is conducted at between 0° and 100°' C., preferably about 60° C.

It will be appreciated that the (R)-4-amino-3-hydroxy butyronitrile formed from hydrazide 10 can be converted back to 3,4-dihydroxy butyric acid with nitrous acid and then heated to form the (R)-lactone 3. This is particularly useful if the (R) butyro lactone is needed. It is a useful intermediate to other compounds.

EXAMPLE 1

(S)-4-Bromo-3-hydroxybutyric acid ethyl ester (5) (FIG. 2, Scheme 1). A mixture of 20.4 g (0.2 mol) of lactone 3, was stirred with 60 ml (0.3 mol) of 30% hydrogen bromide in acetic acid at 60° C. for 4 hours. Ethanol (300 ml) was added to the reaction mixture and it was left stirring at the same temperature for another 4–6 hours. The mixture was concentrated to remove the solvent and ethyl acetate formed during the reaction. The residue was taken up in toluene and treated with 10% sodium bicarbonate solution followed with water until the water phase was neutral. The toluene layer was dried with sodium sulfate and after removal of the solvent, the product ester 5 was obtained as a dark yellow liquid. Yield was 38 g (90%). It can be further purified by Kugelrohr distillation to yield a light yellow oil >95% pure by gas chromatography. $\alpha_D^{598}$=–14.0 (c=1.1, $CHCl_3$) (Lit. 25, $\alpha_D^{598}$=–11, c=1, ethanol) $^1$H-NMR ($CDCl_3$, 300 MHz) δ ppm, 4.20- (m, 1H), 4.17 (q, 2H, J=7.2 Hz), 3.50 (dd, 1H, J=5.1 and 10.5 Hz), 3.45 (dd, 1H, J=5.7 and 10.5 Hz), 2.63 (m, 2H) 1.26 (t, J=7.2 Hz), $^{13}$C-NMR ($CDCl_3$, 75 MHz) 171.7, 67.4, 61.0, 39.3, 37.3, 14.0.

(R)-4-Cyano-3-hydroxybutyric acid ethyl ester (4) (FIG. 2, Scheme 1). The bromoester (5) 42.2 g (0.2 mol) was dissolved in a vigorously stirred 4:1 ethanol/water mixture 80 ml. Where is sodium hydroxide? The solution was heated to 50° C. and 11.8 g (0.24 mol) of NaCN was added. Vigorous stirring was continued at this temperature for 3 hours. The reaction mixture was then cooled, solvent was removed by rotatory evaporation and the residue was extracted with ethyl acetate (300 ml). The ethyl acetate layer was filtered through a celite mixed with silica gel and the solvent was then removed to give the product 4 as a light yellow liquid, yield was 29.8 g (95%). It could be further purified by distillation (b.p. 108° C., 0.5 mm Hg). $\alpha_D^{598}$=–31.3 (c=1.0, $CHCl_3$) (Lit. 19, $\alpha_D^{598}$=–33.1, c=1.2, $CHCl_3$). $^1$H-NMR ($CDCl_3$, 300 MHz) δ ppm, 4.32 (m, 1H), 4.18 (q, 2H, J=7.2 Hz), 2.70–2.50 (m, 4H), 1.26 (t, J=7.2 Hz). (Lit. 19, $^1$H-NMR ($CDCl_3$, 200 MHz) δ 4.36 (m, 1H), 4.19 (q, 2H, J=7.1 Hz), 2.64 (m, 4H), 1.29 (t, J=7.1 Hz).) $^{13}$C-NMR ($CDCl_3$, 75 MHz) 171.3, 117.2, 63.8, 61.0, 40.1, 40.0, 24.9, 13.9.

Figure 3:
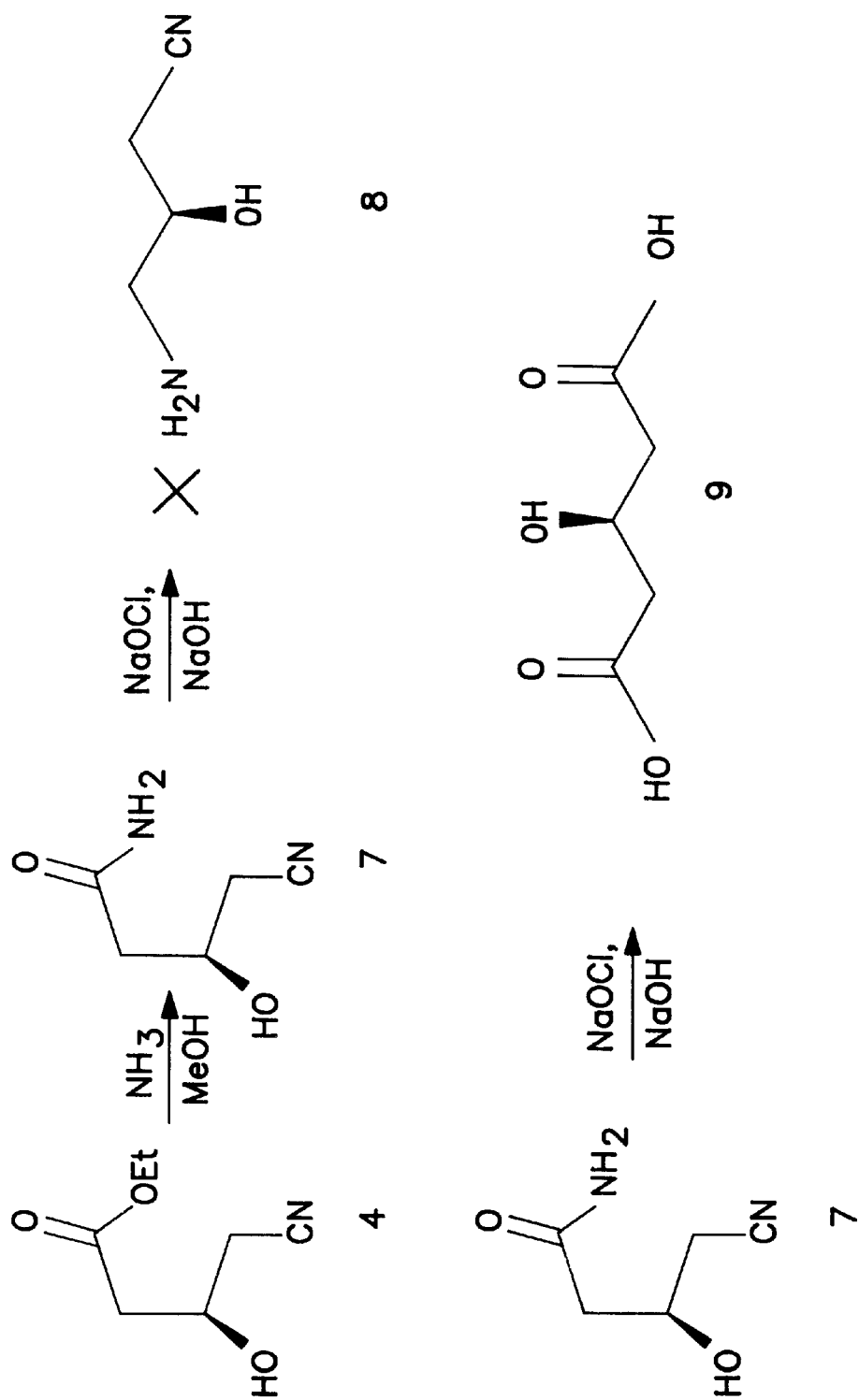
FIG. 3 shows Scheme 2 for the unsuccessful Hoffman rearrangement on the amide and protected amide.

(R)-4-Cyano-3-hydroxybutyramide (7) (FIG. 3, Scheme 2). The cyano ester (4) 15.7 grams (0.10 mol), was stirred with 30% ammonium hydroxide 21 g (0.18 mol) and 20 ml methanol for 10 hours, after which time the reaction was essentially completed. Salts and other ions were removed by passing the mixture through a mixed bed resin (DOWEX MR3) in methanol and water as the eluting solvent. Removal of the solvent gave the amide 7 as a yellow crystalline solid. Yield 10.6 g (83%). M.p. 124–126° C. $\alpha_D^{598}$=–10.6 (c=1.0, MeOH) $^1$H NMR ($D_2O$, 300 MHz) δ ppm, 4.25 (m, 1H), 2.68 (dd, 1H, J=4.8, 17.1 Hz), 2.60 (dd, 1H, J=6.6, 17.1 Hz), 2.36 (d, 2H, J=6.6 Hz). $^{13}$C-NMR ($CD_3OD$, 75 MHz) 176.4, 119.8, 65.1, 42.5, 26.1 IR absorption $cm^{-1}$; 3387, 3100, 1665, 1410, 1208, 1084.

(R)-4-cyano-3-hydroxy butyric acid hydrazide (10) (FIG. 4, Scheme 3). 15.7 grams (0.10 mol) of the cyano ester 4 was dissolved in absolute ethanol (30 ml) and the mixture was added to 4.8 g (0.15 mol) of anhydrous hydrazine in absolute ethanol (10 ml). It was left stirring for 2 hours over which time a white solid precipitated. The white solid was filtered by vacuum filtration and washed twice with 5 ml ethanol and dried. Yield: 14 g (98%), m.p. 134–136° C. $\alpha_D^{598}$=–13.2 (c=1.0, $H_2O$) $^1$H NMR ($D_2O$, 300 MHz) δ ppm 4.24 (m, 1H ), 2.70 (dd, 1H, J=4.5, 17.1 Hz), 2.58 (dd, 1H, J=6.3, 17.1 Hz), 2.36 (m, 2H). $^{13}$C-NMR ($CD_3OD$, 75 MHz) δ ppm 172.4, 119.8, 65.0, 41.3, 26.1, C H N elemental analysis (Galbraith Laboratories, Knoxville, Tenn.) C: 41.89%, H: 6.34%, N: 29.37% (Calc, C: 41.95%, H: 6.34%, N, 29.35%).

(R)-4-amino-3-hydroxybutyronitrile (8) (FIG. 4, Scheme 3). 1.43 g (0.01 mol) of the hydrazide 10 was dissolved in 10 ml water, and 1.2 g concentrated sulfuric acid diluted in 10 ml water was added to the stirred solution. The mixture was cooled in an ice bath and then 1.36 g (0.02 mol) of NaNO$_2$ was added. It was stirred at 60° C. for 14 hours, after which time the reaction was essentially complete as determined by $^1$H NMR spectroscopy (>95% conversion). The reaction mixture was then concentrated to dryness and then taken up in ethanol. It was stirred for 1 hour and filtered to remove salts and other solids. The filtrate was a yellow liquid which upon cooling to room temperature yielded a light yellow crystalline solid. This was redissolved in water and passed down an ion exchange resin (DOWEX-1 chloride form). The water was removed by lyophilization to give the hydrochloride salt of compound 8, the yield was 1.1 g (80%). $^1$H NMR (D$_2$O, 300 MHz) δ ppm 4.90 (m, 1H), 3.73 (dd, J=9.0, 9.9 Hz), 3.30 (dd, 1H, J=5.7, 9.9 Hz), 2.94 (dd, 1H, J=4.2, 17.4 Hz), 2.84 (dd, 1H, J=5.7, 17.4 Hz). δ ppm $^{13}$C-NMR (CD$_3$OD, 75 MHz) δ ppm 117.3, 73.1, 45.8, 23.8. IR (CaF$_2$ cell) cm$^{-1}$, 3306 (broad), 2255, 1491, 1078, $\alpha_D^{598}$=+63.2 (c=1.0, MeOH) (hydrochloride salt). The optical purity of the cyanoamine was determined by chiral HPLC as the 3,4-dinitrobenzoyl derivative. Condition for chiral HPLC: Phenomenex (S)-ICA+R, 250×4.0 mm, mobile phase, hexane:dichloroethane:ethanol=6:3:1, flow rate 0.8 ml/min. The optical purity was greater than 99%.

The chirality of compounds 8, 4, and 10 described herein are:
Compound 8
E. e>99.5% (by chiral HPLC) [α]$_D$=+63.2 (MeOH, c=1, HCl salt). Source of chirality: starting lactone. Absolute configuration: 3R (R)-4-amino-3-hydroxybutanenitrile.
Compound 4
E.e>99% (by chiral HPLC) [α]$_D$=−31.3 (CHCl$_3$, c=1) Source of chirality: starting lactone. Absolute configuration: 3R (R) 4-cyano-3-hydroxy-butyric acid ethyl ester.
Compound 10
[α]$_D$=−13.2 (H$_2$O, c=1) Source of chirality: starting lactone. Absolute configuration: 3R (R)-4-cyano-3-hydroxy butyric acid hydrazide.

In the present invention the R-chiral compounds are preferably produced; however, it will be appreciated that the compounds produced could have (R) and (S) chirality or (S) chirality alone, depending on the stereochemistry of the acylhydrazide. This will be obvious to those skilled in the art.

EXAMPLE 2

1.43 g (0.01 mol) of the hydrazide 10 was dissolved in 10 ml water, and 1.2 g concentrated sulfuric acid diluted in 10 ml water was added to the stirred solution. The mixture was cooled in an ice bath and then 1.36 g (0.02 mol) of NaNO$_2$ dissolved in 10 ml water was added. It was then stirred at room temperature for one hour, about 100 ml of ether or chloroform was added to reaction mixture. The mixture was stirred for an additional one-half hour, the organic layer was isolated and dried by drying reagents such as sodium sulfate. To the filtered organic phase, 1 ml of trifluoroacetic acid was added. Then it was heated to gentle reflux for an additional 6 hours, the solvent was removed, and water was added to the residue. This solution was heated at 60° C. for 4–6 hours after which the conversion to the final product amine salt was completed. The work up was similar to the previous procedure of Example 1.

It is intended that the foregoing description be only illustrative of the present invention and that the present invention be limited only by the hereinafter appended claims.

We claim:
1. 4-Cyano-3-hydroxybutanoyl hydrazide.
2. R-4-Cyano-3-hydroxybutanoyl hydrazide.
3. A process for the preparation of 4-cyano-3-hydroxybutanoyl hydrazide which comprises:
   (a) reacting 4-cyano-3-hydroxybutyric acid alkyl ester, where alkyl contains 1 to 6 carbon atoms, with anhydrous hydrazine in a polar organic solvent to produce the 4-cyano-3-hydroxybutanoyl hydrazide in a reaction mixture; and
   (b) separating the 4-cyano-3-hydroxylbutanoyl hydrazide from the reaction mixture to produce the 4-cyano-3-hydroxybutanoyl hydrazide.
4. The process of claim 1 wherein alkyl is ethyl and the 4-cyano-3-hydroxybutyric acid alkyl ester is the R isomer and the 4-cyano-3-hydroxybutanoyl hydrazide is the R isomer.
5. A process for the preparation of 3-cyano-3-hydroxybutanoyl hydrazide which comprises:
   (a) reacting 4-cyano-3-hydroxybutyric acid alkyl ester, where alkyl contains 1 to 6 carbon atoms, with anhydrous hydrazine in absolute ethanol in the absence of water to produce the 4-cyano-3-hydroxybutanoyl hydrazide in a reaction mixture as a precipitate; and
   (b) separating the precipitate from the reaction mixture to produce the 4-cyano-3-hydroxybutanoyl hydrazide.
6. The process of claim 5 wherein alkyl is ethyl and the 4-cyano-3-hydroxybutyric acid alkyl ester is the R isomer and the 4-cyano-3-hydroxybutanoyl hydrazide is the R isomer.
7. A process for the preparation of 4-amino-3-hydroxybutyronitrile which comprises:
   (a) reacting 4-cyano-3-hydroxy butyric acid alkyl ester, where alkyl contains 1 to 6 carbon atoms, with anhydrous hydrazine in a polar organic solvent to produce 4-cyano-3-hydroxybutanoyl hydrazide in a reaction mixture:
   (b) separating the 4-cyano-3-hydroxybutanoyl hydrazide from the reaction mixture to produce the 4-cyano-3-hydroxybutanoyl hydrazide; and
   (c) reacting 4-cyano-3-hydroxybutanoyl hydrazide with a decarboxylation and rearrangement agent to produce the 4-amino-3-hydroxybutyronitrile as a salt in a reaction mixture; and
   (d) separating the 4-amino-3-hydroxybutyronitrile as a salt from the reaction mixture.
8. The process of claim 7, wherein alkyl is ethyl and, the 4-amino-3-hydroxybutyronitrile, the 4-cyano-3-hydroxybutanoyl hydrazide and the 4-amino-3-hydroxybutyronitrile are the R isomer.
9. A process for the preparation of 4-amino-3-hydroxybutyronitrile which comprises:
   (a) reacting 4-cyano-3-hydroxy butyric acid alkyl ester, where alkyl contains 1 to 6 carbon atoms, with anhydrous hydrazine in absolute ethanol in the absence of water to produce 4-cyano-3-hydroxybutanoyl hydrazide in a reaction mixture as a precipitate;
   (b) separating the precipitate from the reaction mixture to produce the 4-cyano-3-hydroxybutanoyl hydrazide; and
   (c) reacting 4-cyano-3-hydroxybutanoyl hydrazide with nitrous acid to produce the 4-amino-3-hydroxybutyronitrile as a salt in a reaction mixture; and
   (d) separating the 4-amino-3-hydroxybutyronitrile as a salt from the reaction mixture.

* * * * *